United States Patent
Pümpel et al.

(10) Patent No.: US 10,633,269 B2
(45) Date of Patent: Apr. 28, 2020

(54) METHOD FOR DETERMINING THE AMOUNT OF ANAMMOX BACTERIA (71) Applicant: UNIVERSITÄT INNSBRUCK, Innsbruck (AT)

(72) Inventors: Thomas Pümpel, Trins (AT); Sabine Marie Podmirseg, Innsbruck (AT)

(73) Assignee: UNIVERSITAT INNSBRUCK, Innsbruck (AT)

( * ) Notice: Subject to any disclaimer, the term of this patent is extended or adjusted under 35 U.S.C. 154(b) by 385 days.

(21) Appl. No.: 15/505,404

(22) PCT Filed: Aug. 20, 2015

(86) PCT No.: PCT/EP2015/069189
§ 371 (c)(1),
(2) Date: Aug. 29, 2017

(87) PCT Pub. No.: WO2016/026945
PCT Pub. Date: Feb. 25, 2016

(65) Prior Publication Data
US 2018/0009689 A1    Jan. 11, 2018

(30) Foreign Application Priority Data
Aug. 21, 2014 (AT) .................. 50579/2014

(51) Int. Cl.
C02F 3/30 (2006.01)
C02F 1/38 (2006.01)
C12Q 1/06 (2006.01)

(52) U.S. Cl.
CPC .............. *C02F 3/307* (2013.01); *C02F 1/385* (2013.01); *C12Q 1/06* (2013.01); *C02F 2209/36* (2013.01); *C12Q 2304/00* (2013.01)

(58) Field of Classification Search
CPC ...... C02F 3/307; C02F 1/385; C02F 2209/36; C12Q 1/06; C12Q 2304/00
See application file for complete search history.

(56) References Cited

FOREIGN PATENT DOCUMENTS

WO    WO005176 A1    2/2000

OTHER PUBLICATIONS

Ali et al., "The increasing interest of Anammox in China: Bacteria, Process Development, and Application" BioMed Research International, vol. 2013, Article ID 134914, 21 pages.
Berry et al., "Simultaneous Determination of Hemes a, b, and c from Pyridine Hemochrome[1] Spectra", Analytical Biochemistry 161, 1-15, 1987.
Chen et al., "Growth and metabolism characteristics of anaerobic ammonium-oxidizing bacteria aggregates", Appl Microbiol Biotechnol (2013) 97:5575-5583.
Estabrook, "Low temperature spectrum of cytochrome c", 1956, vol. 19, p. 184.
International Search Report cited in PCT Application No. PCT/EP2015/069189 dated Nov. 6, 2015.
Nelson et al., "Alkali-induced reduction of the b-cytochromes in purified Complex III from beef heart mitochondria", 1975, vol. 396, No. 2, pp. 202-209.
Podmirseg et al., "Comparative evaluation of multiple methods to quantify and characterized granular anammox biomass", Water Research 68 (2015), pp. 194-205.
Sinclair, "Measurement of heme concentration", Current Protocols in Toxicology (1999) 8.3.1-8.3.7, 1999.
Tang et al., "Performance of high-loaded Anammox UASB reactors containing granular sledge", Water Research 45 (2011), pp. 135-144.
Wynn et al., "The membrane-bound electron-transfer components of aerobically grown Chromatium vinosum", 1985, vol. 808, pp. 85-93.

*Primary Examiner* — Kade Ariani
(74) *Attorney, Agent, or Firm* — Workman Nydegger (57) ABSTRACT

A method and a kit for determining the amount of anammox bacteria in a bioreactor, comprising the steps of 1) removing a sample from the bioreactor, 2) mixing the sample with alkali, 3) heating the samples to at least 60° C., 4) separating solid components, 5) adding a reducing agent to the liquid phase, 6) measuring the translucence of the liquid phase in a spectrophotometer at three wavelengths ranging from 500 to 600 nm, and 7) comparing the measured translucence to a reference spectrum.

7 Claims, 4 Drawing Sheets

METHOD FOR DETERMINING THE AMOUNT OF ANAMMOX BACTERIA

The present invention relates to a method of determining the amount of anammox bacteria in bioreactors. Furthermore, the invention relates to a kit, in particular for use in such a method.

PRIOR ART

Anammox bacteria are able to convert ammonium ($NH_4^+$) and nitrite ($NO_2^-$) into molecular nitrogen ($N_2$) via anaerobic ammonium oxidation. Therefore, anammox bacteria are used industrially for the removal of nitrogen in wastewater treatment plants. WO 2007/033393 A1 describes a wastewater treatment plant of that kind. Since the operation of a wastewater treatment plant with anammox bacteria is relatively complex, up until recently only wastewaters highly loaded with nitrogen were treated with anammox bacteria. The aim, however, is to employ anammox bacteria also for wastewaters with a low nitrogen load in municipal wastewater treatment plants.

For the optimal operation of wastewater treatment plants with anammox bacteria (=AnAOB anoxic ammonium oxidizing bacteria), a quantitative detection of those microorganisms is important. The reason for this is that anammox bacteria have a very long doubling time of from 11 to 20 days (Jetten et al. 2009), which, in comparison to other bacteria in wastewater treatment plants (e.g., AerAOB (=aerobic ammonium oxidizing bacteria) or NOB (=nitrite oxidizing bacteria)), is a very long period of time (Jetten et al. 2001). While, in case of bacteria with doubling times in the range of hours, disruptive influences have a fast effect, it is also possible to take quick countermeasures against them and to re-establish a state of physiological equilibrium or a steady state, respectively, within the shortest possible time. In anammox bacteria, a disruptive influence on the growth will be noticeable only after days or weeks so that, in most cases, countermeasures are taken too late. Further days or weeks will pass before the number of anammox bacteria in the wastewater treatment plant returns to normal levels after those countermeasures haven been taken so that the wastewater treatment plant will fail to provide an optimal removal of nitrogen for a substantial period of time.

SUMMARY OF THE INVENTION

Thus, it is the object of the present invention to provide a method for enabling to determine the number of anammox bacteria easily so that the condition in a bioreactor, in particular in a wastewater treatment plant, can be monitored.

This object is achieved by a method of determining the amount of anammox bacteria in bioreactors, in particular in clarifying basins, comprising the steps of
   i) removing a sample from the bioreactor, in particular the clarifying basin; then
   iii) mixing the sample with alkali;
   v) heating the samples to at least 60° C.;
   vi) separating solid components;
   vii) adding a reducing agent to the liquid phase; then
   viii) measuring the translucence of the liquid phase in a spectrophotometer at three wavelengths ranging from 500 to 600 nm;
   ix) comparing the measured translucence to a reference spectrum.

In step (i), a representative sample is initially taken.

If the liquid matrix does not produce a considerable measuring fault, which can be detected by preliminary tests, the sample is mixed with an alkali in step (iii). For that purpose, a highly concentrated alkaline solution or solid alkalis can be added directly to the sample in such an amount that the final concentration of $OH^-$ is preferably 1 mol/L. Metal hydroxides are preferably used, which, particularly preferably, are hydroxides of alkali metal ions, in particular NaOH.

If the liquid matrix produces a considerable measuring fault, the additional step (ii) of separating the solid components from the liquid components is performed after step (i) and prior to step (iii). However, this step is only necessary if there are considerable amounts of reddened impurities (wavelength range from 500 nm to 600 nm). The separation of the solid components is effected, for example, by centrifugation. Centrifuge tubes can be used for this. A centrifugation at a centrifugal acceleration of 5,000 g for 3 min has proved to be advantageous. The supernatant is then discarded, and the sample is mixed with an alkali (step (iii)). For this purpose, the sample container is preferably replenished to the original volume, and the solid residue is resuspended.

In step (v), the samples are heated to at least 60° C., preferably at least 70° C., particularly preferably between 90 and 110° C. Preferably, the heating takes places for at least one minute, preferably for about 2 minutes, particularly preferably for about 10 minutes. The heating may also take longer, for example 20 minutes. The heating may occur, for example, in a water bath or in a heating facility such as, e.g., a heating block. It is advantageous to shake the sample vessel and to allow it to cool during or after the heating.

In step (vi), solid components are separated. For this purpose, a centrifugation step may again be provided, for example at a centrifugal acceleration of 5,000 g for 3 min.

The foregoing steps serve for releasing the heme existing in the anammox bacteria into the solution. In the subsequent step (vii), the addition of a reducing agent to the liquid phase occurs. For this purpose, an amount is provided which is sufficient for converting heme essentially completely to the reduced form. It has turned out to be feasible to add 100 µl of a freshly prepared solution of a reducing agent such as sodium dithionite (200 g/L in caustic soda 1 mol/L) to 1 ml of the liquid phase and to mix this in order to reduce the heme. Alternatively, the appropriate amount of reducing agent (e.g. sodium dithionite) may be added in powder form.

In the next step (viii), the measurement of the translucence of the liquid phase is effected in a spectrophotometer at three wavelengths ranging from 500 to 600 nm. In the present case, the extinction of the liquid was measured concretely in the spectrophotometer at 535, 550 and 570 nm. Alternatively, of course, the transmission may also be measured.

In the final step (ix), the comparison of the measured translucence to a reference spectrum is conducted. The actual amount of heme can be inferred therefrom, which is a measure of the presence of anammox bacteria in wastewater.

At 550 nm, for example, the peak height of heme can be calculated relative to the baseline defined by the two measuring points at 535 and 570 nm (3-wavelengths calibration function). For the calibration, any heme protein which has a known heme content can be used, for example, cytochrome c from the heart of a horse (Sigma C-2506; M=12,384 g/mol).

Therefore, it has proved to be convenient if the wavelength measurement of the first wavelength takes place at 530-540 nm, preferably at 535 nm, the second wavelength at 545-555 nm, preferably at 550 nm, and the third wavelength at 565-575, preferably at 570 nm.

Furthermore, it may be envisaged that the separation of the solid components is effected by centrifugation. Additionally or alternatively, a filtration step may be provided for this purpose.

The reducing agent is advantageously a salt of a dithionous acid, preferably $Na_2S_2O_4$.

The present invention provides an efficient and simple method for the indirect quantification of anammox bacteria. In this process, the method makes use of the fact that anammox bacteria exhibit a large amount of heme proteins. The heme content in turn correlates with the activity of anammox bacteria and can thus be used as an indirect measurand for the quantification.

In contrast to methods for the quantification of heme as they are already known from the field of medicine (Sinclair et al., Curr Protoc Toxicol. 2001 May; Chapter 8: Unit 8.3), the present method has been optimized for anammox bacteria. The invention optimizes the method of Sinclair et al. in that two steps are omitted. Firstly, the derivatization of heme with pyridine is omitted, secondly, the oxidation of the heme and a subsequent comparative measurement of oxidized and reduced heme are omitted.

In the present case, the extraction of heme from anammox bacteria has been optimized in terms of liquor strength, temperature and exposure time. In the method as proposed by Sinclair et al., a derivatization of heme is effected with toxic pyridine. Such is not required in the present method. Instead of the determination of optical differential spectra of oxidized and reduced heme as it is also applied by Sinclair et al., the easier measurement of only the reduced heme at—preferably three—wavelengths is suggested.

The sequence of the steps iii) (and optionally ii)) to vii) can also be varied, whereas step i) has to be performed prior to steps ii) to vii), and steps viii) to ix) have to be performed after steps ii) to vii).

This means that the mixing of the sample with alkali may also occur after the addition of the reducing agent to the liquid phase; the heating may also be effected, for example, after the addition of a reducing agent and alkali. Preferably, however, the separation of solid components occurs after the addition of alkali and/or a reducing agent.

Therefore, the method according to the invention is feasible in any standard laboratory with a conventional spectrophotometer. In order that the measurement can be performed also in a wastewater treatment plant just with a simple laboratory equipment, furthermore a kit comprising a sample vessel, an alkaline solution, a reducing agent and a spectrophotometer, which is operable at least at three wavelengths ranging from 500 to 600 nm, is proposed according to the invention.

Additionally, said kit can be characterized by a heating facility.

Furthermore, the kit may comprise a separating device for solid substances. For example, this could be a filter or a centrifuge.

The chemicals required for the kit can also be submitted. Thus, the handling steps required during use are reduced. In one design variant, is it therefore envisaged that the kit comprises a—preferably closed—sample vessel, in which an alkali or an alkaline solution is submitted.

Further, it may be envisaged that the kit comprises a—preferably closed—sample vessel in which the reducing agent is submitted.

Preferably, the sample vessel, in which the reducing agent is submitted, is a cuvette for the spectrophotometer.

The determination of the activity and, respectively, the biomass of anammox bacteria in laboratories of wastewater treatment plants is currently possible only to a limited extent. For the application in the main stream of a wasterwater treatment plant, the established methods such as the determination of conversion rates or a gravimetric analysis are unsuitable, since alternative materials conversions proceed at least equivalently and, thus, superimpose the anammox activity. The analysis of specific ingredients for estimating the activity and, respectively, the biomass of anammox bacteria such as heme or DNA has so far been reserved for appropriately equipped research laboratories and thus has been unsuitable for daily on-site monitoring. The present invention provides the advantage that a quantification via heme determination can be performed in any standard wastewater treatment laboratory without much effort. Thus, the invention allows anammox bacteria to be monitored on site in a routine laboratory, requires only standard chemicals and standard equipment, respectively, and is therefore substantially more economical than the analysis through specialized laboratories. By continuous monitoring, malfunctions can be detected early and countermeasures can be initiated.

DETAILED DESCRIPTION AND EXAMPLES

COMPARISON OF DIFFERENT METHODS OF DETERMINING THE MASS OR ACTIVITY OF ANAMMOX BACTERIA

Due to physiological and morphological characteristics which, in part, are very exceptional, the following very diverse examination methods come into consideration:
  quantification of functional or phylogenetic genes with molecular-biological techniques
  chemical-analytical quantification of characteristic cell ingredients such as membrane components, especially ladderanes measurement of the characteristic physiological activity, in particular of the conversion of ammonium with nitrite to molecular nitrogen and nitrate quantification and measurement of the typical granular structures of anammox bacteria.

Despite the variety of analytical possibilities, today almost only the molecular-biological techniques and the measurement of physiological activity are applied. However, particularly for routine monitoring in a wastewater treatment plant, meaningful, reliable and robust methods, which still can be performed easily on site using standard equipment, are not provided for the control of the anammox population.

Samples from the wastewater treatment plant Strass im Zillertal (AT) were examined by six different methods, the results were statistically evaluated, and the characteristics of the methods, in particular their advantages and disadvantages, were compared to:
1. gravimetric analysis of anammox granules (GA)
2. quantification of the heme content (HQ)
3. counting and measuring the granules with a Coulter Counter (CC)
4. counting and measuring the granules using image analysis (PT)
5. DNA extraction and quantitative polymerase chain reaction (qPCR)
6. physiological activity measurement (AM)

Material and Methods

Samples, Sampling and Sample Pretreatment

In line with this invention, samples from the wastewater treatment plant Strass im Zillertal were examined. The samples come from different plant sections and therefore differ significantly with respect to their sample matrix:

a) DEMON® Anammox Treatment Technology reactor, treats digested-sludge press water highly loaded with nitrogen, contains large amounts of anammox bacteria b) aeration basin in the main stream which has been doped with anammox biomass from the DEMON® Anammox Treatment Technology reactor since 2011. Municipal wastewater with a relatively low nitrogen load is treated there, the anammox bacteria have a far lower concentration in comparison to other populations of bacteria.

In addition, at each plant, three different fractions were taken from the respective installed hydrocyclone: i) cyclone inflow (=reactor contents), ii) cyclone underflow (=enriched anammox fraction which is recycled to the reactor), iii) cyclone overflow (=depleted anammox fraction, withdrawn excess sludge).

TABLE 1 sample designations

| Plant | fraction | sample designation |
|---|---|---|
| DEMON ® Anammox Treatment Technology | basin | SL |
| | cyclone overflow | SL-OF |
| | cyclone underflow | SL-UF |
| main stream | aeration basin | B |
| | cyclone overflow | B-OF |
| | cyclone underflow | B-UF |

From each sample, 3 parallels of 1 L each were taken representatively. The further sample division for the various analyses was performed in a thoroughly mixed stirrer vessel in order to prevent especially the rapid sedimentation of the granular biomass (vessel with baffles, Rushton stirrer). Depending on the method, the subsamples were deep-frozen until the examination (qPCR), stored at 4° C. (GA, CC, PT) or examined immediately on the same day (AM, HQ).

Gravimetric Analysis (GA)

The mass of substances capable of being filtered off was determined by filtration through glass fiber filters (Macherey & Nagel GF5) and drying overnight at 105° C. The loss on ignition as a measure of the organic portion was analyzed after 3 h at 550° C.

In the samples from the DEMON® Anammox Treatment Technology reactor, the anammox granules were sieved in the wet state through an analysis sieve with a mesh size of 0.125 mm, dried and weighed. For the main stream samples, this was not possible because of the slimy biomass.

Quantification of the Heme Content (HQ)

1.5 mL each of the samples were centrifuged in 2 mL micro reaction vessels for 3 min at 5000 g. The supernatant was discarded and replaced by 1 M NaOH. The pellet was resuspended, the vessels were placed in boiling water for 2 minutes and subsequently allowed to cool for 10 min, while occasionally being shaken up. Residual particles were centrifuged at 5000 g for 3 min, and 1 mL of a clear supernatant was transferred to semi-micro photometer cuvettes. For the reduction of the extracted heme, 100 µL of a freshly prepared solution of sodium dithionite (200 g/L in 1 M NaOH) was mixed in.

After 5 minutes, the extinctions were measured at 535, 550 and 570 nm with a spectrophotometer. The peak at 550 nm was related to the baseline, which is defined by the extinctions at 535 and 570 nm.

The analysis was calibrated with cytochrome c from the heart of a horse (contains 1 heme per molecule; Sigma C-2506).

Calculation of the peak height at 550 nm:

$$\text{Peak height}(AU) = E_{bb0} - E_{b35} - \frac{E_{570} - E_{535}}{570\text{ nm} - 535\text{ nm}} * (550\text{ nm} - 535\text{ nm})$$

$E_{535}$, $E_{550}$, $E_{570}$ . . . measured extinctions (AU) at the respective wavelength Counting and Measuring the Granules Using the Image Analysis Method "Particle Tracking" (PT)

Samples of 15 mL each were filled into petri dishes, and those were recorded against a homogeneous white background with a flatbed scanner at a resolution of 600 dpi. The samples were diluted to such an extent that no superpositions of particles appeared in the image.

The images were processed with an image analysis program (Fiji) such that the anammox granules could be detected separately because of their color difference to the background and to other particles. The identified granules were counted and the cross-sectional area of each granule was calculated. The number of granules and the sum of the cross-sectional areas were related to the employed sample volume and used as a measure of the anammox biomass.

Counting and Measuring the Granules with a Coulter Counter (CC)

As an alternative to the image evaluation, a particle analyzer was also used according to the Coulter principle (Coulter 1956). The particles are thereby sucked through a measuring opening and the increase in the electrical resistance of the opening, which occurs as a result of the narrowing of the cross-section, is measured and evaluated. In contrast to the image analysis, the Coulter Counter detects only that volume of a particle which is electrically isolated from the surrounding electrolyte. Bacterial slimes and cavities of anammox granules are not detected in this way, but rather the sum of intact cells.

In a sample-isotonic saline solution, the samples were diluted to such an extent that always only individual particles get sucked through the opening. The measurements were carried out using a Multisizer II (Coulter Beckman Inc.) having a measuring tube with a measuring opening of 1000 µm.

Size calibration was effected with spherical styrene-divinylbenzene particles having a modal diameter of 320 µm.

DNA Extraction and Quantitative Polymerase Chain Reaction (qPCR)

The quantitative polymerase chain reaction (qPCR) was used for determining the number of 16 S rRNA gene copies. Beforehand, the DNA was extracted by means of the DNeasy® Blood & Tissue Kit according to the "Pretreatment for Gram-Positive Bacteria" protocol (QIAGEN; manual 07/2006). In order to increase the total DNA yield, three freeze-thaw cycles (liquid nitrogen/65° C. water bath; 5 minutes each) were also conducted at the beginning. A mechanical digestion was additionally included after the chemical lysis according to the manufacturer's instructions (20 mg/mL lysozyme and proteinase K), wherein the sample was transferred into PowerBead vessels (MO BIO Laboratories, Inc.) and was shaken in a horizontal shaker at 60 Hz for 4 minutes. Subsequently, the sample was centrifuged at 8000 g for 3 minutes and the protocol was continued. The final elution occurred in 100 µL AE buffer (heated to 60° C.) in two consecutive steps (2×50 µL).

Physiological Activity Measurement (AM)

The metabolic activity of anammox bacteria was quantified as a conversion rate of the sum of the three essential dissolved nitrogen species ammonium, nitrite and nitrate, for which the following reaction equation is applicable if conditions are undisturbed:

$NH_4^+ + 1.32\ NO_2^- 0.132\ HCO_3^- + 0.512\ H^+ \Rightarrow 1.02\ N_2 + 0.26\ NO_3^- + 0.132\ CH_2O_{0.5}N_{0.15} + 2.19\ H_2O$ The samples to be examined were adjusted to sufficient initial concentrations of the substrates ($NH_4$: 100 mg N/L with $NH_4HCO_3$, $NO_2$: 70 mg N/L with $NaNO_2$), and the pH was adjusted to 7.2. 100 mL were each filled into 100 mL Erlenmeyer flasks, which were sealable in a gas-tight manner, and the dissolved oxygen was driven out by the injection of nitrogen gas. The vessels were sealed and incubated at 30° C. while being shaken. 1 mL samples were taken over a total of 4 h at intervals of 30 min, they were centrifuged, and the concentrations of nitrite, nitrate and ammonium were measured in the supernatant (in each case with Nanocolor Kits from Macherey & Nagel). The concentrations were added up per measuring point (in mg N/L), and, from the linear area of the temporal concentration gradient, the slope was calculated which was used as a measure of the activity (volumetric N-conversion rate in mg N/(L.h.)). In addition, the specific N-conversion rate was calculated with reference to the biomass dry matter contained in the sample (mg N/(L.h.g. TS)).

Statistical Analyses

All statistical analyses were performed with the software PAST (Version 2.17) (Hammer et al. 2001). The separation of the various sample types using all the examined methods was illustrated with reference to a non-metric multidimensional scaling. For this purpose, the data were log-transformed, and the Bray-Curtis index was used. The correlation between the different methods was illustrated by a MANTEL permutation analysis, based on Bray-Curtis distance matrices, for each method and for all sample types. In order to check the reproducibility of the heme method, the coefficient of variation (CV(%)) was determined, and the mean values were calculated for every sample matrix and compared to each other.

Results

General Comparison Between the Six Employed Methods

Table 2 summarizes all analytical findings and additional data regarding the individual sample types (dry matter (TS), organic dry matter (oTS), number of granules). The deeply reddened AC granules (Anammox Consortium: AnAOB, AerAOB and other potential microbial groups which may also be aggregated in the granules, such as NOB and Chloroflexi) from the wastewater treatment plant Strass exhibit a relatively heterogeneous structure. Cryotome sections show that the interior of those granules consists largely of cavities (data not shown).

Due to the sample selection and the density fractionation using hydrocyclones in the plants, the following basic sequence of the samples in terms of the anammox biomass may be assumed: SL-UF > SL > SL-OF > B-UF > B > B-OF (anammox is much more active in the DEMON® Anammox Treatment Technology reactor (SL) than in the main stream (B), and, in each case, there is an anammox accumulation in the cyclone underflow). This hypothesis had to be confirmed with the employed methods.

Figure 1:
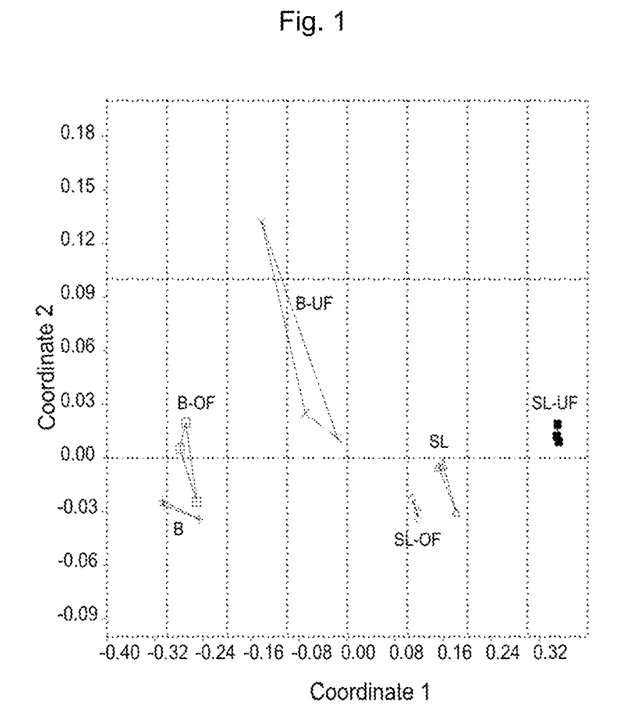
FIG. 1 shows the non-metric multidimensional scaling of the AC/AnAOB biomass quantification for six types of samples, SL, SL-OF, SL-UF, B, B-OF and B-UF. For the calculation, all six quantitative methods, GA, PT, HQ, AM, qPCR and CC, were included. Samples from the same group (parallels) are connected through lines which reflect the convex enveloping surface of the NM-MDS results.

All six methods were capable of distinguishing between the different sample matrices and hydrocyclone fractions (non-metric multidimensional scaling (NM-MDS), FIG. 1). A lower stress value of <0.02 indicated a realistic depiction of the original data in the NM-MDS. The $R^2$ values were 0.99 (coordinate 1) and, respectively, 0.00007 (coordinate 2). It became evident that the SL samples could be distinguished from each other better than, for example, the samples B and B-OF, for which an overlap occurred along the x-axis ($R^2$=0.99). All in all, samples which, in general, contained more anammox biomass (SL matrix) could be separated better.

Looking individually at the results of all six methods, it became apparent that all were able to categorize the SL samples correctly, whereas, for the B matrix, this was possible only by means of qPCR and HQ (Table 3). The quantification by means of CC was carried out only for the SL matrix, since the separation of the granules from the activated sludge turned out to be very complex for B samples. In order to check the reproducibility and, respectively, the variance of the heme method, the coefficient of variation was determined. Thereby, it was shown that the average CV was roughly the same for both sample matrices, namely 4.45 (SL) and, respectively, 5.20 (B), and therefore this method yielded data of similar reproducibility in substantially different sample matrices.

Looking at all the methods in terms of their suitability for quantifying only AnAOB biomass, it becomes apparent that the qPCR approach aimed at the 16 S rRNA of Planctomycetales is the most accurate method. However, should one wish to determine the AC biomass, HQ, PT and CC are similarly suitable. In comparison to the CC approach, the PT method has the advantage of an additional color selection and, hence, a better identification of AC granules, whereby this method is also suitable for more complex matrices, e.g., activated sludge with embedded granules. In addition to the quantification of the AC biomass, both methods provide an additional qualitative evaluation of the size distribution of the granules. Based on three false classifications of the samples, the GA was classified as the least precise method (see Table 3).

Table 4 summarizes the most important advantages and disadvantages of each method and provides further information on the average duration of the measurements, detection limits, and the price per analysis.

In Tables 5, 6 and 7, the results of the correlation analyses between all methods are shown, which can be summarized as follows: the highest correlation was achieved for the SL matrix, with significant Pearson correlation coefficients for all methods >0.71. Excluding the qPCR method, even values >0.96 are obtained. Looking at both sample matrices jointly, significantly positive correlations are still obtained, albeit with a somewhat lower Pearson coefficient (0.30-0.96). The highest correlation was obtained between GA and PT, the lowest values with AM. The analysis of the B matrix provided significantly high positive correlations (all >0.94; CC not examined) for GA, PT and HQ and significantly reduced, but positive correlations for qPCR (0.41-0.47). For the AM, no positive correlation was achieved in the B matrix, a fact which is examined more closely in the chapter "Physiological Activity".

In sum, the correlation analysis is supposed to serve as a guideline to understand which methods group the examined samples in a similar way. However, this does not imply the correctness of the results. Nevertheless, HQ and qPCR were the only methods which were able to divide the sample set as expected (see Table 3), and both methods achieved a correlation coefficient of 0.81. Therefore, a high correlation of a different method with those two methods also suggests a higher accuracy of the results.

Additional observations made on samples from other wastewater treatment plants are indicated hereinbelow. These results are indicative of a high applicability of the employed methods to other sample matrices: i) samples from a DEMON® Anammox Treatment Technology basin of a different wastewater treatment plant contained red and black anammox granules; these could be divided into two fractions based on their different densities and were analyzed by means of AM and HQ. Both methods indicated a high activity and heme concentration in the red fraction and drastically reduced values in the black fraction. This suggests that, due to the color selection, HQ and PT can be used not only for the quantification, but also for the activity measurement. ii) In a further wastewater treatment plant, which also carries out sidestream deammonification using DEMON® Anammox Treatment Technology technology and, in addition, features two completely separate biological sludge lines, an anammox biomass was enriched in one of those lines, and the second line was left untreated as a control. In the control line, only few anammox granules could be detected by PT (less than 0.1%-1%, as compared to the results of the B samples (this study), whereas anammox granules were clearly detected in the bio-augmented line. iii) Heme proteins are ubiquitous in nature (Gumiero et al. 2011), but the measured HQ values in samples from wastewater treatment plants not operating an additional deammonification process were still below the detection limit. This indicates a reduced risk of false positive results with this method.

TABLE 3 summary of the sample division by the six employed methods, as compared to the expected sample sequence; differences in this sequence are marked grey;

| Sample designation | expected AC/AnAOB abundance* | GA | PT | HQ | AM | qPCR | CC |
|---|---|---|---|---|---|---|---|
| SL | 2 | 2 | 2 | 2 | 2 | 2 | 2 |
| SL-OF | 3 | 3 | 3 | 3 | 3 | 3 | 3 |
| SL-UF | 1 | 1 | 1 | 1 | 1 | 1 | 1 |
| B | 5 | 5 | 6 | 5 | 6 | 5 | n.a. |
| B-OF | 6 | 5 | 5 | 6 | 5 | 6 | n.a. |
| B-UF | 4 | 3 | 4 | 4 | 4 | 4 | n.a. |
| AnAOB specifity | accuracy for exclusive AnAOB measurement | 6 | 3 | 2 | 5 | 1 | 4 |

* figures reflect the ranked, expected AC/AnAOB abundance, with 1 representing the highest and 6 the lowest abundance; figures in the lowermost line are ranked from 1 (best suited method) to 6 (least suited method),
n.a. . . . not analyzed;

TABLE 2 sample characterization by means of TSS, VSS; granular SS (particles >0.125 mm diameter), $PT_{tot}$ cross-sectional area (entire sample), $PT_{sieved}$ cross-sectional area (particles >0.125 mm and <1 mm diameter), $PT_{tot}$ (particle count entire sample), $PT_{sieved}$ (particle count >0.125 mm and <1 mm diameter), CC (AC volume of granules sieved samples >0.125 mm and <1 mm diameter), HQ, qPCR, AM (total nitrogen conversion), rate of $NH_4$—N, $NO_2$—N and $NO_3$—N formation; mean values (bold) and standard deviation; n = 3 (for CC n = 9 (3 technical parallels)), n.a. = not analyzed;

| | SS [g L$^{-1}$] | VSS [g L-1] | GA granular r-SS [g L$^{-1}$]* | $PT_{tot}$ cross-sectional area [mm$^2$ L$^{-1}$] | $PT_{sieved}$ cross-sectional area [mm$^2$ L$^{-1}$] sieved | $PT_{tot}$ [particle L$^{-1}$] | $PT_{sieved}$ [particle L$^{-1}$] | CC [mL L$^{-1}$] | HQ [mAU L$^{-1}$] | qPCR [gene copies L$^{-1}$] | AM [mg N L$^{-1}$*h$^{-1}$] | NH$_4$ [mg NH$_4$—N L$^{-1}$ h$^{-1}$] | NO$_2$ [mg NO$_2$—N L$^{-1}$ h$^{-1}$] | NO$_3$ [mg NO$_3$—N L$^{-1}$ h$^{-1}$] |
|---|---|---|---|---|---|---|---|---|---|---|---|---|---|---|
| SL | 2.95 | 2.32 | 0.79 | 283 | 280 | 326267 | 297600 | 40 | 164 | 9.32E+11 | −36.1 | −17.2 | −22.7 | 3.72 |
| | 0.09 | 0.07 | 0.12 | 35.6 | 33.2 | 36116 | 32822 | 0.94 | 12.2 | 7.50E+11 | 4.51 | 4.27 | 0.77 | 0.24 |

TABLE 2-continued sample characterization by means of TSS, VSS; granular SS (particles >0.125 mm diameter), $PT_{tot}$ cross-sectional area (entire sample), $PT_{sieved}$ cross-sectional area (particles >0.125 mm and <1 mm diameter), $PT_{tot}$ (particle count entire sample), $PT_{sieved}$ (particle count >0.125 mm and <1 mm diameter), CC (AC volume of granules sieved samples >0.125 mm and <1 mm diameter), HQ, qPCR, AM (total nitrogen conversion), rate of $NH_4$—N, $NO_2$—N and $NO_3$—N formation; mean values (bold) and standard deviation; n = 3 (for CC n = 9 (3 technical parallels)), n.a. = not analyzed;

| | SS [g L$^{-1}$] | VSS [g L-1] | GA granular r-SS [g L$^{-1}$]* | $PT_{tot}$ cross-sectional area [mm$^2$ L$^{-1}$] | $PT_{sieved}$ cross-sectional area [mm$^2$ L$^{-1}$] sieved | $PT_{tot}$ [particle L$^{-1}$] | $PT_{sieved}$ [particle L$^{-1}$] | CC [mL L$^{-1}$] | HQ [mAU L$^{-1}$] | qPCR [gene copies L$^{-1}$] | AM [mg N L$^{-1}$*h$^{-1}$] | NH$_4$ [mg NH$_4$—N L$^{-1}$ h$^{-1}$] | NO$_2$ [mg NO$_2$—N L$^{-1}$ h$^{-1}$] | NO$_3$ [mg NO$_3$—N L$^{-1}$ h$^{-1}$] |
|---|---|---|---|---|---|---|---|---|---|---|---|---|---|---|
| SL-OF | 2.19 | 1.77 | 0.44 | 131 | 129 | 184400 | 160933 | 35.8 | 86.4 | 7.01E+11 | −23.1 | −10.8 | −14.6 | 2.22 |
| | 0.06 | 0.05 | 0.00 | 11.3 | 11.2 | 9165 | 8259 | 1.61 | 7.03 | 2.48E+11 | 2.20 | 1.39 | 1.15 | 0.24 |
| SL-UF | 8.95 | 6.59 | 4.69 | 4985 | 4965 | 4249333 | 3958667 | 113 | 1143 | 3.72E+12 | −115 | −71.3 | 54.7 | 10.9 |
| | 0.51 | 0.32 | 0.19 | 984 | 997 | 691449 | 490067 | 3.00 | 8.68 | 1.19E+12 | 2.33 | 2.95 | 1.93 | 0.52 |
| B | 4.25 | 3.05 | 0.07 | 3.62 | 3.46 | 8533 | 6000 | N.a. | 12.3 | 4.00E+09 | −0.45 | 3.65 | −4.11 | 0.01 |
| | 0.61 | 0.44 | 0.01 | 0.55 | 0.66 | 462 | 2227 | | 0.33 | 1.27E+08 | 2.83 | 2.53 | 0.31 | 0.01 |
| B-OF | 4.20 | 3.03 | 0.07 | 5.97 | 4.21 | 47333 | 13600 | N.a. | 11.6 | 2.70E+09 | −1.20 | 2.57 | −3.78 | 0.01 |
| | 0.09 | 0.07 | 0.01 | 0.94 | 0.82 | 3585 | 1600 | | 0.51 | 4.03E+08 | 2.43 | 2.64 | 0.55 | 0.01 |
| B-UF | 6.71 | 4.53 | 0.79 | 32.3 | 50.1 | 113200 | 76000 | N.a. | 25.1 | 2.88E+10 | −3.23 | 4.00 | −7.22 | −0.01 |
| | 0.11 | 0.06 | 0.10 | 16.6 | 16.4 | 22087 | 18543 | — | 2.14 | 4.45E+10 | 2.77 | 1.18 | 1.70 | 0.02 |

TABLE 4 summary of the employed methods and their suitability for AC/AnAOB quantification

| Method | methodical background | advantages | disadvantages | detection limit | suitability for granular and non-granular biomass | time required per sample* | additional demand for laboratory equipment | price per sample (material cost) |
|---|---|---|---|---|---|---|---|---|
| GA | mass determination of granular biomass >0.125 mm diameter; | fast, cheap, small demand for equipment | not applicable to the smallest fraction (<0.125 mm); imprecise; sieve clogging due to (slimy) main stream sludge | not defined | only granular biomass | 5-10 min | analysis sieves, drying balance or drying chamber | <0.50 € |
| PT | particle count/ determination of cross-sectional area by image analysis; | exact granular AC abundance and biomass area/volume**; size distribution of granules; small demand for equipment | red*** colour of granules necessary for activated sludge matrix; | with conventional flatbed scanner particle diameter of approx. 50 μm; | only granular biomass | 10 min | flatbed scanner, image analysis software | <0.50 € |
| HQ | extraction and colorimetric determination of the haemochrom | relatively fast; exact; cheap; measures esp. AnAOB; small demand for equipment | none are known | protocol was adapted such that measurements were possible in both sample matrices | arbitrary | 5-10 min | standard centrifuge, water bath or heating block, photometer | 1-2 € |
| AM | sum of NO$_2$, NO$_3$, H$_4$—N wastage/production rates; | measures activity, not only presence; | distortion due to presence of denitrifying bacteria and ammonification (B); | not defined; incubation time can be prolonged if rates are low | arbitrary | 6 h | specific equipment for commercial kits (photometer) or alternative analysis equipment | approx. 50 € (with commercial kits) |
| qPCR | 16S rRNA gene quantification; | AnAOB specific; if based on RNA, suitable also as an activity parameter | extraction bias; specific equipment required; | 1.2 10$^4$ gene copies per L; | arbitrary, but suitable extraction protocol is important | 8-10 h/3 h**** | molecular- biological laboratory equipment, PCR cycler, qPCR cycler | approx. 10-15 € |
| CC | determination of particle count/volume; granules are assigned | exact granular AC abundance and volume**; | specific equipment required; dependent on sample matrix; | ideal size of granules 2%- 60% of the | only granular | 30-45 min | Coulter Counter | <1 € |

TABLE 4-continued summary of the employed methods and their suitability for AC/AnAOB quantification

| Method | methodical background | advantages | disadvantages | detection limit | suitability for granular and non-granular biomass | time required per sample* | additional demand for laboratory equipment | price per sample (material cost) |
|---|---|---|---|---|---|---|---|---|
| | to size channels; | size distribution of granules; | | measuring opening (here diameter of 1000 μm); | | | | |

*approximate time required for one sample; dependent on the employed method, the total time required for several samples is usually less than a multiple of this specified time.
**the Coulter Counter provides the net biomass volume, whereas Particle Tracking provides the gross volume;
***here, the red colour is the discriminating factor, but other colours or grey scales (darker, denser granules as compared to activated sludge) may also be used as a factor, and the protocol can be modified accordingly;
****the first time also includes the generation of the standards and the DNA extraction, the second only the qPCR run;

TABLE 5 correlation of the AC/AnAOB quantification results between all the examined methods for all six sample types (both sample matrices); Pearson correlation coefficients are indicated along with the respective significance levels (exponent); exponents defined as follows: a ($p < 0.01$), b ($p < 0.001$) and c ($p < 0.0005$);

| | GA | PT sieved | PT total | HQ | qPCR | AM |
|---|---|---|---|---|---|---|
| GA | — | $0.95^c$ | $0.94^c$ | $0.71^c$ | $0.54^b$ | $0.37^b$ |
| PT sieved | $0.95^c$ | — | $0.99^c$ | $0.78^c$ | $0.69^c$ | $0.49^c$ |
| PT total | $0.94^c$ | $0.99^c$ | — | $0.78^c$ | $0.68^c$ | $0.53^c$ |
| HQ | $0.71^c$ | $0.78^c$ | $0.78^c$ | — | $0.81^c$ | $0.30^a$ |
| qPCR | $0.54^b$ | $0.69^c$ | $0.68^c$ | $0.81^c$ | — | $0.38^c$ |
| AM | $0.37^b$ | $0.49^c$ | $0.53^c$ | $0.30^a$ | $0.38^c$ | — |

TABLE 6 correlation of the AC/AnAOB quantification results between all the examined methods for the SL sample matrix; Pearson correlation coefficients are indicated along with the respective significance levels (exponent); exponents defined as follows: a ($p < 0.01$), b ($p < 0.001$) and c ($p < 0.0005$);

| | GA | PT sieved | PT total | HQ | qPCR | AM | CC |
|---|---|---|---|---|---|---|---|
| GA | — | $0.99^c$ | $0.99^c$ | $0.99^c$ | $0.75^b$ | $0.99^c$ | $0.96^c$ |
| PT sieved | $0.99^c$ | — | $1^c$ | $1^c$ | $0.73^b$ | $0.99^c$ | $0.98^c$ |
| PT total | $0.99^c$ | $1^c$ | — | $0.99^c$ | $0.73^b$ | $0.99^c$ | $0.98^c$ |
| HQ | $0.99^c$ | $1^c$ | $0.99^c$ | — | $0.71^b$ | $0.99^c$ | $0.97^c$ |
| qPCR | $0.75^b$ | $0.73^b$ | $0.73^b$ | $0.71^b$ | — | $0.75^b$ | $0.72^b$ |
| AM | $0.99^c$ | $0.99^c$ | $0.99^c$ | 0.99 | $0.75^b$ | — | $0.96^c$ |
| CC | $0.96^c$ | $0.98^c$ | $0.98^c$ | $0.97^c$ | $0.72^b$ | $0.96^c$ | — |

TABLE 7 correlation of the AC/AnAOB quantification results between all the examined methods for the B sample matrix; Pearson correlation coefficients are indicated along with the respective significance levels (exponent); exponents defined as follows: a ($p < 0.05$), b ($p < 0.001$) and c ($p < 0.0005$);

| | GA | PT sieved | PT total | HQ | qPCR | AM |
|---|---|---|---|---|---|---|
| GA | — | $0.99^b$ | $0.97^b$ | $0.99^b$ | $0.44^a$ | −0.15 |
| PT sieved | $0.99^b$ | — | $1^c$ | $0.96^a$ | $0.47^a$ | −0.12 |
| PT total | $0.97^b$ | $1^c$ | — | $0.94^a$ | $0.45^a$ | −0.06 |
| HQ | $0.99^b$ | $0.96^a$ | $0.94^a$ | — | $0.41^a$ | −0.17 |
| qPCR | $0.44^a$ | $0.47^a$ | $0.45^a$ | $0.41^a$ | — | −0.20 |
| AM | −0.15 | −0.12 | −0.06 | −0.17 | −0.20 | — |

Gravimetric Analysis of Anammox Granules (GA)

If anammox granules are present in a high density, the biomass is not too slimy and the amount of particulate impurities in the ratio is low, this simple determination (sieving, washing, drying, weighing) can be used for monitoring. Depending on the size distribution of the granules and the impurities, the mesh size of the sieve can be adjusted. In the case examined herein, the different fractions could be distinguished correctly with a 0.125 mm sieve in the DEMON® Anammox Treatment Technology basin (SL samples) and correlated with the anammox activity.

Quantification of the Heme Content (HQ)

Hemes act as prosthetic groups of many enzymes in all life forms (Gumiero et al. 2011). Particularly high heme contents cause reddening of the cells, such as in case of red blood cells and anammox bacteria. Within the latter, they are an essential component of the metabolic pathway of the anaerobic ammonium oxidation, the enzymes of which can constitute up to 20% of the total protein content of those cells (Jetten et al., 2009), while the heme content in other microorganisms is almost negligible by way of contrast. Thus, the heme content of the biomass of a wastewater treatment plant is a specific parameter for the indirect determination of the content of anammox bacteria and, respectively, their relevant enzymes. The determination of heme for the analysis of medical samples such as, e.g., feces or tissue has been known for quite some time (Sinclair et al. 2001), but had to be optimized to be applied to bacteria.

A correlation between an optically visible reddening of the anammox biomass and its metabolic activity has already been observed on several occasions (separate studies and (Ali et al. 2013)), in particular that very brightly coloured granules as well as granules dyed dark including black show a significantly reduced performance. In combination with optical methods (PT), the analysis of the heme content of the biomass is a simple but safe method of monitoring the abundance and vitality of the anammox population on site.

Counting and Measuring the Granules with a Coulter Counter (CC) and Using Image Analysis (PT)

Those two methods differ from all others in that, in addition to the quantification parameters for the anammox biomass, namely number of granules (CC and PT), total cross-sectional area of granules (PT) and total volume of granules (CC and PT), also size distributions of the particles are detected. This information is relevant, for example, if the growth and composition of the biomass is to be assessed (Nielsen et al. 2005, Volcke et al. 2010, Winkler et al. 2011) or the mode of operation of the hydrocyclones is to be examined in detail.

Quantitative PCR (qPCR)

The fact that all previously known anammox bacteria belong to the same monophyletic order Planctomycetales facilitates their molecular-biological quantification via specific 16 S rRNA primers (Kuenen 2008, Li and Gu 2011). The method provides, on the one hand, the highest possible specificity and therefore essentially the highest correctness for the biomass determination, but involves also some potential sources of error, in addition to the large expenditure. In particular the standard protocol for DNA extraction from gram-positive bacterial cells had to be modified significantly and supplemented with mechanical cell lysis steps in order to achieve a sufficient stable DNA yield from the granular biomass.

Physiological Activity Measurement (AM)

The conversion rates of the essential dissolved nitrogen species ammonium, nitrite and nitrate are often used for evaluating the physiological activity of anammox bacteria, regardless of their growth form. In this connection, it could be shown that this method is very well suited for sewage sludges with high contents of anammox, as they are common in the DEMON® Anammox Treatment Technology reactor. In samples with a high amount of other microorganisms, such as in the examined anammox-enriched main stream basin, the measurements are often hard to interpret due to the superposition by other metabolic processes. In particular denitrification and ammonification (Wett et al. 2013) have the most disturbing effect there, often cause the anammox activity to be underestimated strongly, and, so far, it has not been possible to selectively inhibit them to a sufficient degree. Especially in the cyclone overflow, the ratio of depleted anammox biomass to any other biomass is very inconvenient and renders an activity measurement virtually impossible.

CONCLUSIONS

Using all methods which have been examined herein for the assessment of the anammox biomass or its nitrogen conversion performance, the three different samples from the DEMON® Anammox Treatment Technology reactor (basin, cyclone overflow and underflow) could be distinguished and ranked correctly. Heme determination and PCR were best suited for examining the samples from both reactors (DEMON® Anammox Treatment Technology and main stream).

By means of the methods qPCR and Coulter Counter, which involve more material costs and are reserved for research laboratories, the results and the reliability of the less demanding techniques Particle Tracking and heme determination, which are feasible in every routine laboratory, could be confirmed. Basically all methods were positively correlated, in particular the sample with the highest anammox content yielded the highest values in all methods.

In summary, the following monitoring strategy is proposed for wastewater treatment plants with anammox technology: Regular heme determination and Particle Tracking perfectly complement the abundance and vitality control of anammox bacteria. Occasionally, activity tests should also be performed.

Optimization of the Heme Extraction and Determination from Anammox Bacteria

Figure 2:
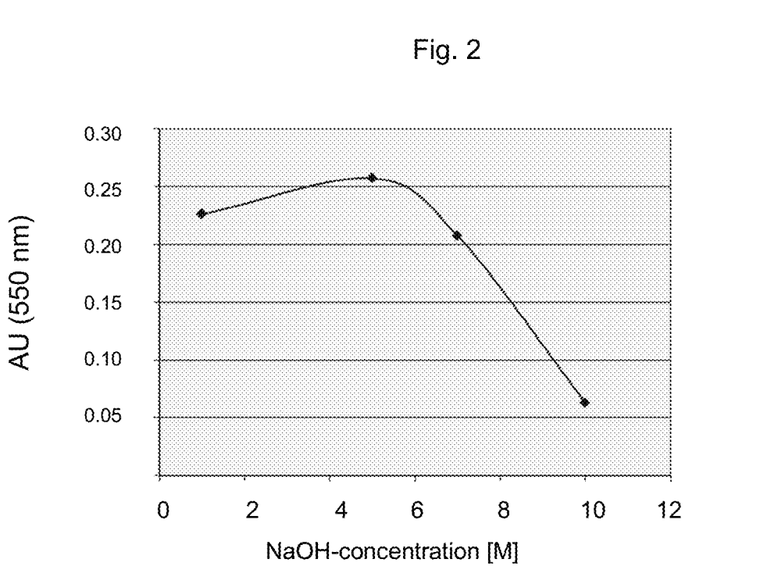
FIG. 2 shows the influence of the NaOH concentration on the yield of heme from an anammox biomass (digestion time of 4 min).
Figure 3:
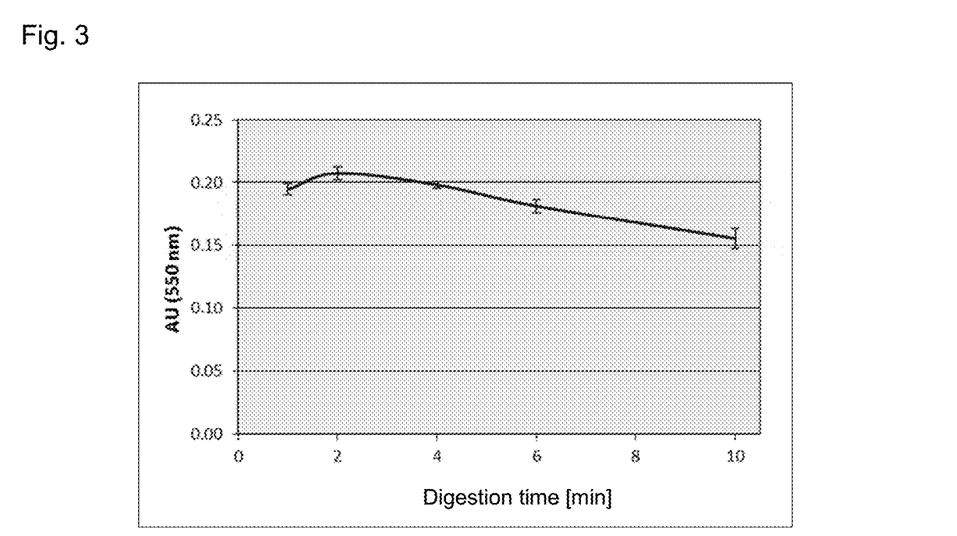
FIG. 3 shows the time course of the heme extraction from an anammox biomass in 1 M NaOH at 100° C.

The optimization of the heme extraction was performed with an anammox biomass from the DEMON® Anammox Treatment Technology reactor Strass im Zillertal and tested at several other facilities. From the test series with regard to liquor strength (FIG. 2) and digestion time (FIG. 3), the optimal combination of degree of digestion and time insensitivity was determined with a NaOH concentration of 1 mol/L and a digestion time of 2 min at 100° C. in a 1.5 mL micro reaction vessel in boiling water. For varying volumes and, respectively, heating techniques (e.g., thermoblock), the optimal digestion time has to be redetermined.

Figure 4:
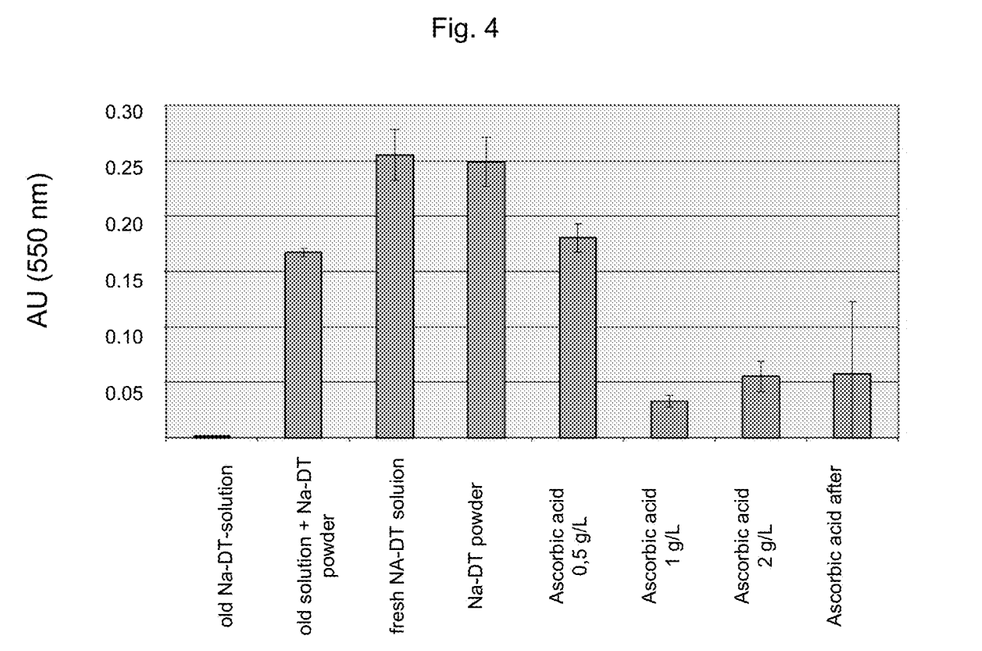
FIG. 4 shows the optimization of species, age and concentration of the reducing agent (sodium DT=sodium dithionate).
Figure 5:
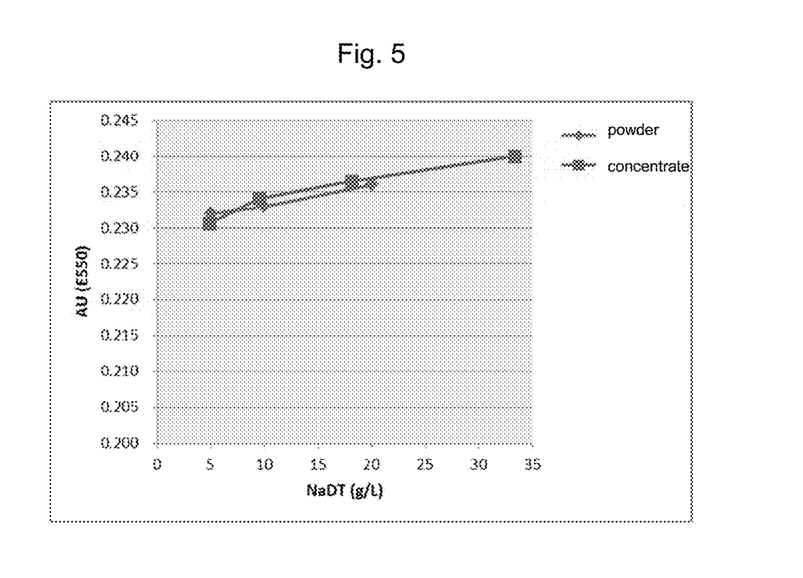
FIG. 5 shows the addition of sodium dithionate as a powder or freshly dissolved in 1 M NaOH, respectively, with the final concentration being the same in each case.

FIG. 4 shows the significance of the addition of a freshly prepared sodium dithionite solution (old=older than 24 hours; fresh=younger than 2 hours). Ascorbic acid is unsuitable as a reducing agent. Instead of a NaDT solution in 1 M NaOH, the reagent may also be added as a powder (FIGS. 4-5).

Figure 6:
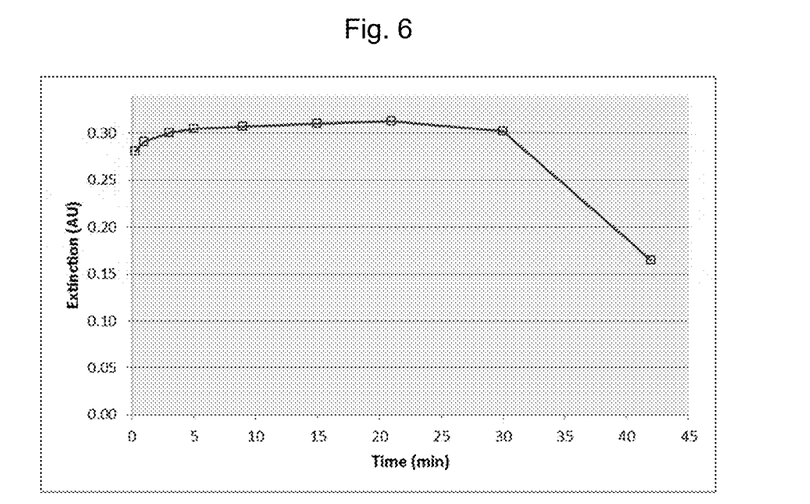
FIG. 6 shows the stability of the haemochrom following a reduction with NaDT.

After extraction and reduction, the red dye remains stable for about 20 min and can be measured photometrically during that time without any significant change (FIG. 6). The peak of the reduced haemochrom at 550 nm can be determined optimally by measuring at 3 wavelengths. Via the measuring points at 535 and 570 nm, the baseline is established and the peak height at 550 nm is based thereupon (3-wavelengths calibration of every modern photometer).

Figure 7:
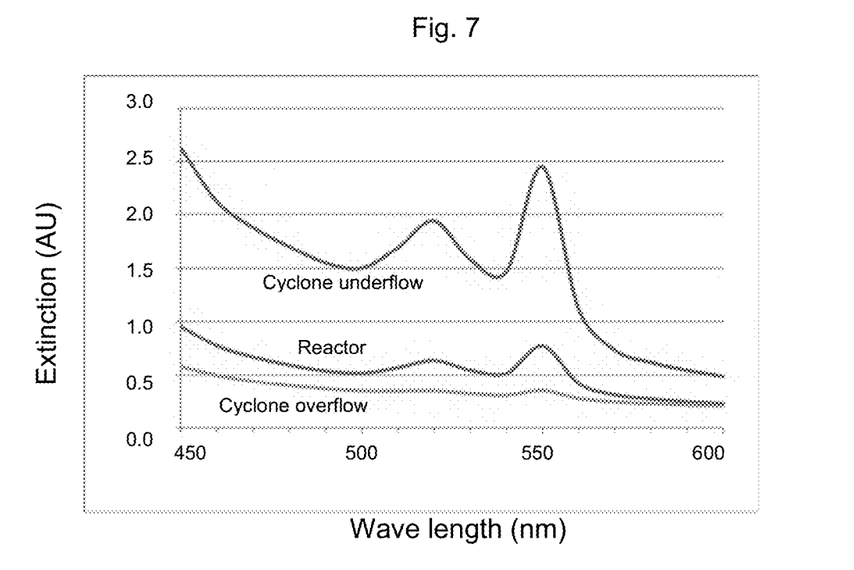
FIG. 7 shows an exemplary measurement on the DEMON® Anammox Treatment Technology reactor of the wastewater treatment plant Tobl/Bruneck and demonstrates the enrichment of the anammox biomass in the cyclone underflow.

FIG. 7 exemplifies the results from samples of the cyclone inflow (=reactor), underflow and overflow of the DEMON® Anammox Treatment Technology reactor of the wastewater treatment plant Tobl/Bruneck (the purpose of the hydrocyclone is to keep the anammox biomass in the reactor via the cyclone underflow and to remove the surplus amount of less dense, faster growing nitrifying and heterotrophic bacterial biomass from the reactor via the cyclone overflow.)

An example of the implementation looked like this, for instance:

Step 1: sampling
Step 2: filling approx. 8-10 mL of the sample into a small tube from the kit in which approx. 200 mg sodium dithionite is submitted in the dry state
Step 3: adding approx. 1 mL caustic soda from the kit (concentration approx. 10-11 mol/L) so that the final concentration in the mixture is 1 mol/L
Step 4: heating the sealed tubes to 70° for 10 min
Step 5: allowing cooling to room temperature
Step 6: filtering and mixing in empty cuvettes (in the kit round cuvettes made of glass such as in other Nanocolor tests)
Step 7: measuring the filtrate in the spectrophotometer.

REFERENCES

Ali, M., Chai, L. Y., Tang, C. J., Zheng, P., MM, X. B., Yang, Z. H., Xiong, L. and Song, Y. X. (2013) The increasing interest of ANAMMOX research in China: bacteria, process development, and application. Biomed Res Int 2013, 134914.

Coulter, W., H. (1956) High Speed Automatic Blood Cell Counter and Cell Size Analyses. Proceedings of the National Electronics Conference 112, 10341040.

Gumiero, A., Metcalfe, C. L., Pearson, A. R., Raven, E. L., Moody, P. C. E. (2011) Nature of Ferryl Heme in Compounds I and II. J Biol Chem 286(20), 1260-1268.

Hammer, O., Harper, D. and Ryan, P. (2001) Paleontological Statistics Software Package for Education and Data Analysis. Palaeontologia Electronica 4, 1-9.

Jetten, M. S., Wagner, M., Fuerst, J., van Loosdrecht, M., Kuenen, G. and Strous, M. (2001) Microbiology and application of the anaerobic ammonium oxidation ('anammox') process. Curr Opin Biotechnol 12(3), 283-288.

Jetten, M., Van Niftrik, L. and Strous, M. (2009) Biochemistry and molecular biology of anammox bacteria. Critical Reviews in Biochemistry and Molecular Biology 44, 65-84.

Kuenen, J. G. (2008) Anammox bacteria: from discovery to application. Nature Reviews Microbiology 6(4), 320-326.

Li, M. and Gu, J. D. (2011) Advances in methods for detection of anaerobic ammonium oxidizing (anammox) bacteria. Appl Microbiol Biotechnol 90(4), 1241-1252.

Mantel, N. (1967) The detection of disease clustering and a generalized regression approach. Cancer Res 27(2), 209-220.

Mantel, N. and Valand, R. S. (1970) A technique of nonparametric multivariate analysis. Biometrics 26(3), 547-558.

Nielsen, M., Bollmann, A., Sliekers, O., Jetten, M., Schmid, M., Strous, M., Schmidt, I., Larsen, L. H., Nielsen, L. P. and Revsbech, N. P. (2005) Kinetics, diffusional limitation and microscale distribution of chemistry and organisms in a CANON reactor. FEMS Microbiol Ecol 51(2), 247-256.

Sinclair, P. R., Gorman, N. and Jacobs, J. M. (2001) Measurement of heme concentration. Curr Protoc Toxicol Chapter 8, Unit 83.

Volcke, E. I., Picioreanu, C., Baets, B. D. and Loosdrecht, M. C. (2012) The granule size distribution in an anammox-based granular sludge reactor affects the conversion—implications for modelling. Biotechnol Bioeng.

Volcke, E. I. P., Picioreanu, C., De Baets, B. and van Loosdrecht, M. C. M. (2010) Effect of granule size on autotrophic nitrogen removal in a granular sludge reactor. Environmental Technology 31(11), 1271-1280.

Wett, B., Omani, A., Podmirseg, S. M., Han, M., Akintayo, O., Gomez Brandon, M., Murthy, S., Bott, C., Hell, M., Takacs, I., Nyhuis, G. and O'Shaughnessy, M. (2013) Going for mainstream deammonification from bench to full scale for maximized resource efficiency. Water Sci Technol 68(2), 283-289.

Winkler, M. K. H., Kleerebezem, R., Kuenen, J. G., Yang, J. J. and van Loosdrecht, M. C. M. (2011) Segregation of Biomass in Cyclic Anaerobic/Aerobic Granular Sludge Allows the Enrichment of Anaerobic Ammonium Oxidizing Bacteria at Low Temperatures. Environmental Science & Technology 45(17), 7330-7337.

The invention claimed is:

1. A method of determining the amount of anammox (anaerobic ammonium oxidation) bacteria in a bioreactor, comprising the steps of:
   i) removing a sample from the bioreactor;
   ii) optionally, separating solid components from liquid components to obtain a supernatant, if reddened impurities in a wavelength range from 500 nm to 600 nm are present, wherein the supernatant is discarded;
   iii) mixing the sample with alkali hydroxide;
   iv) optionally suspending the solid components in the alkali hydroxide;
   v) heating the samples to at least 60° C.;
   vi) separating solid components;
   vii) adding a salt of a dithionous acid as a reducing agent to the liquid phase;
   viii) omitting derivatization of heme with pyridine and oxidation of the heme and a subsequent comparative measurement of oxidized and reduced heme
   x) measuring the translucence of the liquid phase in a spectrophotometer at three wavelengths ranging from 500 to 600 nm, wherein the wavelength measurement of the first wavelength takes place at 530 to 540 nm, the second wavelength at 545 to 555 nm, and the third wavelength at 565 to 575 nm;
   ix) comparing the measured translucence to a reference spectrum of a heme protein with known heme content.

2. The method according to claim 1, wherein separation of the solid components is effected by centrifugation.

3. The method according to claim 1, wherein the salt of dithionous acid is $Na_2S_2O_4$.

4. The method according to claim 1, wherein the bioreactor is a clarifying basin.

5. The method according to claim 1, wherein the wavelength measurement of the first wavelength takes place at 535 nm.

6. The method according to claim 1, wherein the wavelength measurement of the second wavelength takes place at 550 nm.

7. The method according to claim 1, wherein the wavelength measurement of the third wavelength takes place at 570 nm.

* * * * *